(12) United States Patent
Kasahara et al.

(10) Patent No.: US 6,923,759 B2
(45) Date of Patent: Aug. 2, 2005

(54) ENDOSCOPE-COVERING SHEATH AND BLOOD VESSEL HARVESTING APPARATUS USING THE SAME

(75) Inventors: Hideyuki Kasahara, Musashino (JP); Takahiro Kogasaka, Hino (JP)

(73) Assignee: Olympus Corporation, Tokyo (JP)

( * ) Notice: Subject to any disclaimer, the term of this patent is extended or adjusted under 35 U.S.C. 154(b) by 200 days.

(21) Appl. No.: 10/328,236

(22) Filed: Dec. 23, 2002

(65) Prior Publication Data

US 2003/0139649 A1 Jul. 24, 2003

(30) Foreign Application Priority Data

Dec. 28, 2001 (JP) .................................... 2001-401937

(51) Int. Cl.[7] .................................................. A61B 1/12
(52) U.S. Cl. ..................................... 600/157; 600/121
(58) Field of Search ................................ 600/121, 123, 600/125, 133, 153, 155, 156–158, 169

(56) References Cited

U.S. PATENT DOCUMENTS

| | | |
|---|---|---|
| 3,145,249 A | 8/1964 | Meltzer |
| 5,392,766 A | 2/1995 | Masterson et al. |
| 5,518,502 A * | 5/1996 | Kaplan et al. ............... 600/157 |
| 6,755,782 B2 * | 6/2004 | Ogawa ....................... 600/127 |

FOREIGN PATENT DOCUMENTS

| | | |
|---|---|---|
| EP | 1 210 904 A2 | 6/2002 |
| EP | 1 323 382 A1 | 7/2003 |
| JP | 58-61723 | 4/1983 |
| JP | 62-176817 | 11/1987 |
| JP | 08-029699 | 2/1996 |

OTHER PUBLICATIONS

English language abstract of Japanese Laid–Open Patent Application Publication No. Hei 08–029699, published Feb. 2, 1996.

* cited by examiner

*Primary Examiner*—Beverly M. Flanagan
(74) *Attorney, Agent, or Firm*—Scully, Scott, Murphy & Presser

(57) ABSTRACT

An elongated sheath body for an endoscope has a channel provided in the sheath body to allow the endoscope to be inserted into the sheath body. The endoscope channel has a first opening at a distal end of the sheath body and a second opening at a proximal end of the sheath body. The endoscope-covering sheath is provided with a wiper provided near the first opening and a mechanism which drives the wiper. The wipers can wipe adhering matter which hinders the viewing field of the endoscope.

21 Claims, 17 Drawing Sheets

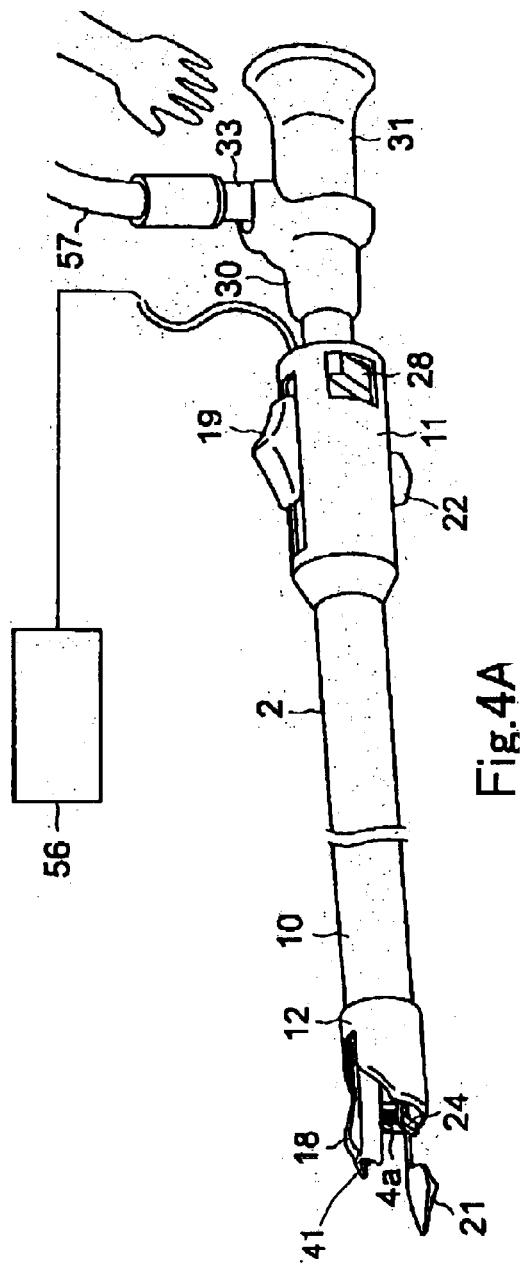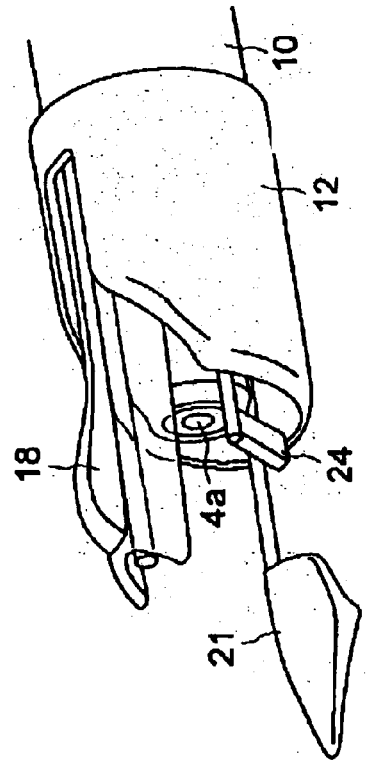
Fig.4A
Fig.4B

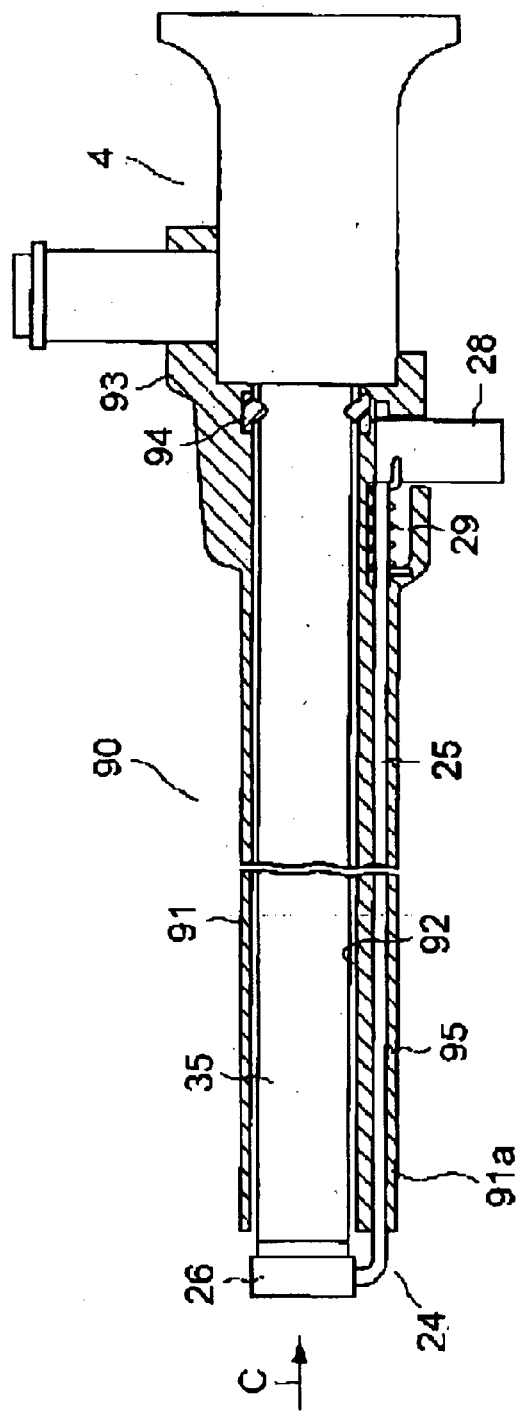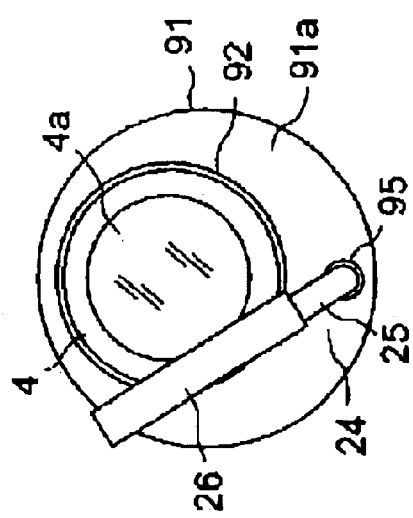
Fig.18A
Fig.18B

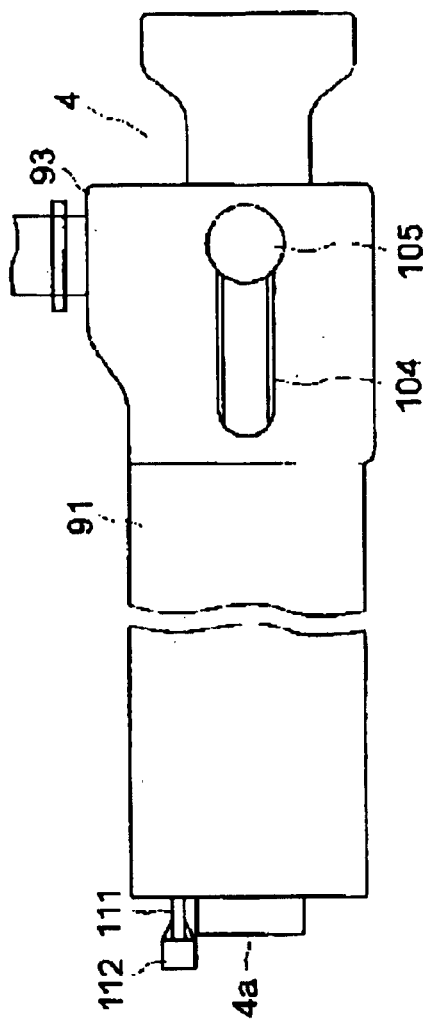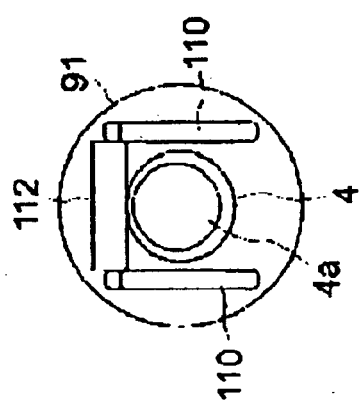
Fig.21A
Fig.21B

ENDOSCOPE-COVERING SHEATH AND BLOOD VESSEL HARVESTING APPARATUS USING THE SAME

CROSS-REFERENCE TO RELATED APPLICATION

This application claims benefits of Japanese Patent Application No. 2001-401,937, filed on Dec. 28, 2001, in Japan, the contents; of which are hereby incorporated by reference.

BACKGROUND OF THE INVENTION

1. Field of the Invention

This invention relates to an endoscope-covering sheath used for endoscopic blood vessel harvesting which endoscopically harvests a subcutaneous blood vessel such as a great saphenous vein.

2. Description of the Related Art

A cannula and a surgical method that are used for endoscopically pulling and harvesting a subcutaneous blood vessel such as a great saphenous vein are known in, for example, PCT/US99/31242 and Laid-Open Japanese Patent Application No. 2000-37,389.

The cannula is a straight tubular device having an instrument inserting passage in its inside, and a manipulating portion is provided at the proximal end of the cannula. A traction device, a rigid endoscope and dissecting forceps are removably inserted in the instrument inserting passage of the cannula from the end of the manipulating portion. The traction device has at its distal end a loop portion that projects from the tip of the cannula and makes an angle with the axial direction of the cannula.

When a subcutaneous blood vessel, such as a great saphenous vein, is to be endoscopically harvested by using the cannula, the following surgical method is adopted. Namely, referring to FIG. 23, when an operator is to harvest the entire length of a harvesting target blood vessel (hereinafter referred to as a blood vessel) C such as a great saphenous vein which extends from the upper portion of the inguinal region A of the thigh of a lower limb 1000 to an ankle B, the operator dissects, for example, A portion of skin E1, E2 or E3 at the upper portion of the inguinal region A, the knee D and the ankle B respectively immediately above the blood vessel C by means of a scalpel or the like.

The operator exposes the blood vessel C in the area of the dissected portion of skin E1, E2 or E3 by means of a dissector 3 or the like. Further, the operator parts tissue immediately above the blood vessel C by means of the same or similar dissector over a distance from the dissected portion of skin E1, E2 or E3, such that the blood vessel is observable with the naked eyes.

FIG. 24 is a cross-sectional view taken along line 24—24 of FIG. 23. Reference numeral 1001 denotes skin, reference numeral 1002 denotes a subcutaneous tissue, and reference numeral 1003 denotes a connective tissue of the blood vessel. The blood vessel C exists under the connective tissue 1003 of the blood vessel. First of all, the operator uses as a dissector a cannula having a conical tip secured to its cannula tip and forms a cavity G from the surrounding tissue to separate it from the blood vessel C. In the following description, reference will be made to the harvesting of the blood vessel C which extends between the dissected portion of skin E2 of the knee D and the inguinal region A. The operator removes the conical tip from the tip of the cannula, and inserts the cannula into the cavity G through the dissected portion of skin E2 and inserts the cannula toward the dissected portion of skin E1 of the knee D along the top portion of the blood vessel C while observing through a rigid endoscope.

In the course of inserting the cannula into the cavity G, while the operator is repeatedly moving the traction device back and forth by manipulating a manipulating portion disposed at the proximal end of the cannula, the operator holds the blood vessel C with the loop portion disposed at the distal end of the cannula and separates from the blood vessel C the subcutaneous tissue 1002 and the connective tissue of blood vessel 1003, and cuts a plurality of side branch vessels F which branch off from an intermediate portion of the blood vessel C, with the dissecting forceps. The operator repeats this manipulation to harvest the blood vessel C extending between the dissected portion of skin E2 and the inguinal region A.

When the cannula is forced into the cavity G, adhering matter such as blood, mucosa and subcutaneous fat existing in the cavity adheres to the objective lens surface of the endoscope and hinders the viewing field of the endoscope. In addition, the cannula has a structure in which the traction portion and the dissecting forceps are removably inserted through the sheath, and the operator performs manipulation with the traction device and the dissecting forceps projected from the sheath.

Accordingly, after adhering matter such as blood, mucosa and subcutaneous fat existing in the cavity adheres to the traction device and the dissecting forceps, when the traction portion and the dissecting forceps are retracted into the sheath, adhering matter such as blood, mucosa and subcutaneous fat adheres to the objective lens surface of the endoscope and hinders the viewing field of the endoscope.

For this reason, in the related art, when the viewing field of the endoscope is hindered, the operator temporarily stops operations, pulls the endoscope out of the sheath, and wipes the objective lens surface, and again inserts the endoscope into the sheath. However, this leads to the problem that operation time is prolonged.

To solve this problem, it is known that as disclosed in Laid-Open Japanese Patent Application No. Hei 8-29,699, a wiper for wiping an objective lens surface is provided on the end surface of the casing of an objective lens in an endoscope and the wiper is driven by a motor provided in the interior of the casing of the objective lens.

In addition, as disclosed in Laid-open Japanese utility Model Application No. Sho 62-176,817, it is know that in an endoscope of the type in which an observation window and an illuminating window are arranged adjacently in the axial direction in the tip portion (along the length) of the endoscope, a wiper is constructed to move axially back and forth along the tip portion of the endoscope to wipe the observation window and the illuminating window.

However, the former endoscope is constructed to drive the wiper by electric power, and needs a complicated structure and an increased cost. The former endoscope also has the problem that since a motor is contained in the casing of the objective lens, the tip of the endoscope is large in diameter. The latter endoscope has a structure that allows the wiper to move axially back and forth along the tip portion of the endoscope by a handle being rotated back and forth by an operator-side manipulating portion, that is, a structure that transforms rectilinear motion into rotary motion, so that speedy manipulation is impossible. In addition, the driving system is complicated and entails a cost increase.

SUMMARY OF THE INVENTION

This invention provides an endoscope-covering sheath in which during manipulation, even if mucosa, blood, subcutaneous fat or similar matter existing in a cavity adheres to an observation window, such adhering matter can be easily removed.

An endoscope-covering sheath according to this invention includes an elongated sheath body, and an endoscope channel provided in the sheath body to allow an endoscope to be inserted into the sheath body, the endoscope channel having a first opening at a distal end of the sheath body and a second opening at a proximal end of the sheath body, and a wiper provided near the first opening. In the endoscope-covering sheath, when the endoscope is inserted into the endoscope channel, the tip portion of the endoscope can be wiped at a position near the first opening.

In this invention, since the wiper is provided on the endoscope-covering sheath, the body of the endoscope does not become thick.

In addition, during manipulation, even if mucosa, blood, subcutaneous fat or similar matter existing in the cavity adheres to the observation window, the surface of the observation window can be wiped.

The endoscope-covering sheath according to the invention is suited for reducing manipulation time.

Other features and advantages of this invention will become apparent from the following detailed description of the examples when taken in conjunction with the accompanying drawings and appended claims.

BRIEF DESCRIPTION OF THE DRAWINGS

FIG. 4A is a perspective view of the endoscope-covering sheath through which the rigid endoscope is inserted, in the first example and FIG. 4B is an enlarged perspective view of the tip portion shown in FIG. 4A;

FIGS. 18A and 18B show a second example of the invention, FIG. 18A being a longitudinal sectional side view of an endoscope-covering sheath, and FIG. 18B being a front view of the endoscope-covering sheath as viewed in the direction of arrow C;

FIGS. 21A and 21B show a fifth example of the invention, FIG. 21A being a side view of an endoscope-covering sheath, and FIG. 21B being a front view of the endoscope-covering sheath;

DETAILED DESCRIPTION OF THE EXAMPLES OF THE INVENTION

Figure 1:
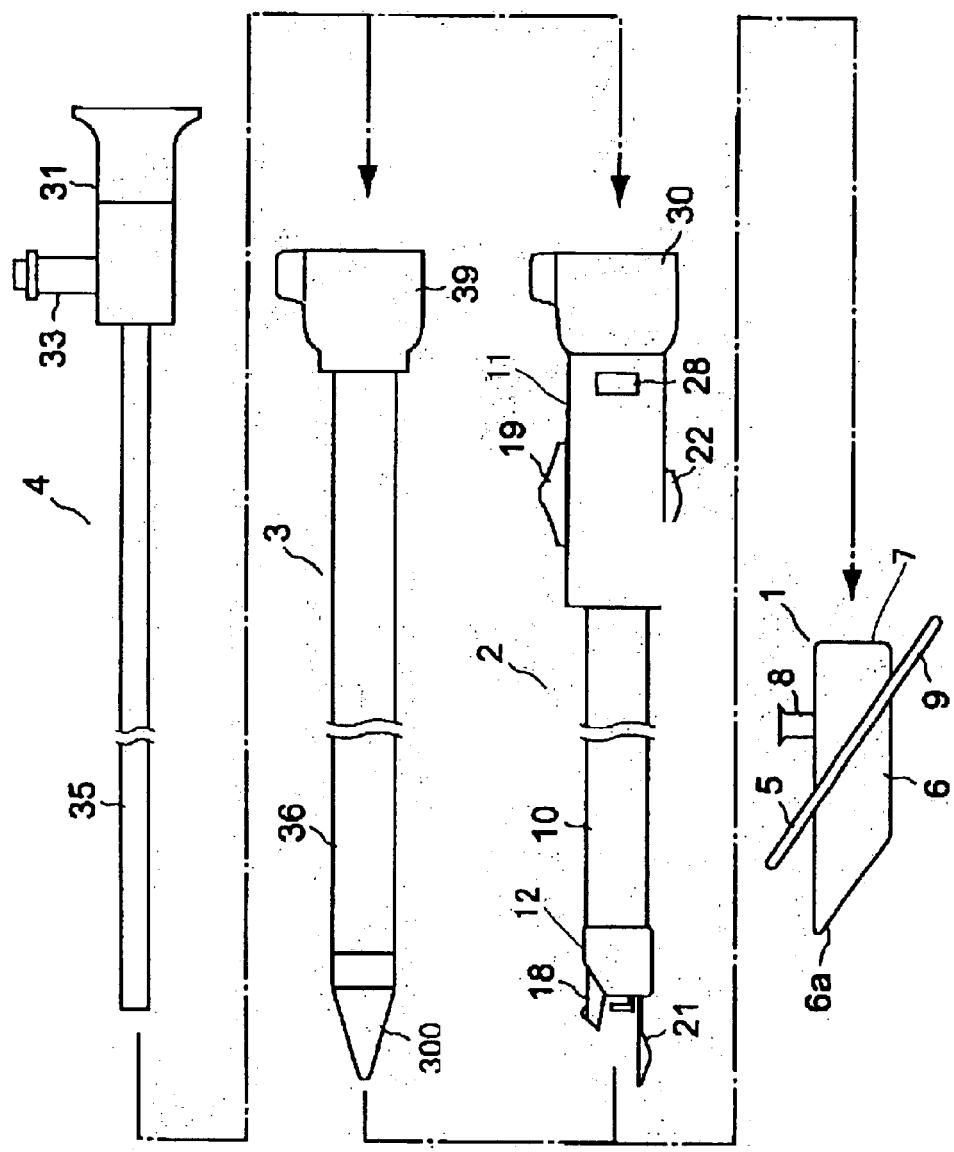
FIG. 1 is a side view of a blood vessel harvesting apparatus according to A first example of this invention.

FIGS. 1 to 17 show a first example of the invention. FIG. 1 shows an endoscopic blood vessel harvesting apparatus for use in endoscopic blood vessel harvesting operation. This endoscopic blood vessel harvesting apparatus includes a trocar 1, an endoscope-covering sheath 2, a dissector 3 which serves as expanding means, and an endoscope 4. In this example, a rigid endoscope is used as the endoscope 4.

The trocar 1 is formed as an integral object, from a synthetic resin material or the like, and a cylindrical guide tube 6 is obliquely inserted through a flange 5 having an approximately disk-like shape. The outer surface of the guide tube 6 is covered with a lubricating coating for improving the smoothness of insertion. The tip 6a of this guide tube 6 is cut at an acute angle, and the end surface of the tip 6a is formed approximately in parallel with the flange 5.

In addition, the inner circumferential surface of the proximal end of the guide tube 6 is integrally provided with an gastight ring 7, and an intermediate portion of the guide tube 6 is integrally provided with, a gas feed connecting portion 8. In addition, the bottom surface of the flange 5 is provided with an adhesive layer 9 such as adhesive tape, and the trocar 1 can be adhesively fixed to the skin of a patient. A detailed description of the trocar 1 is provided in co-pending U.S. application Ser. No. 10/328,237, the contents of which is incorporated herein by reference.

Figure 2:
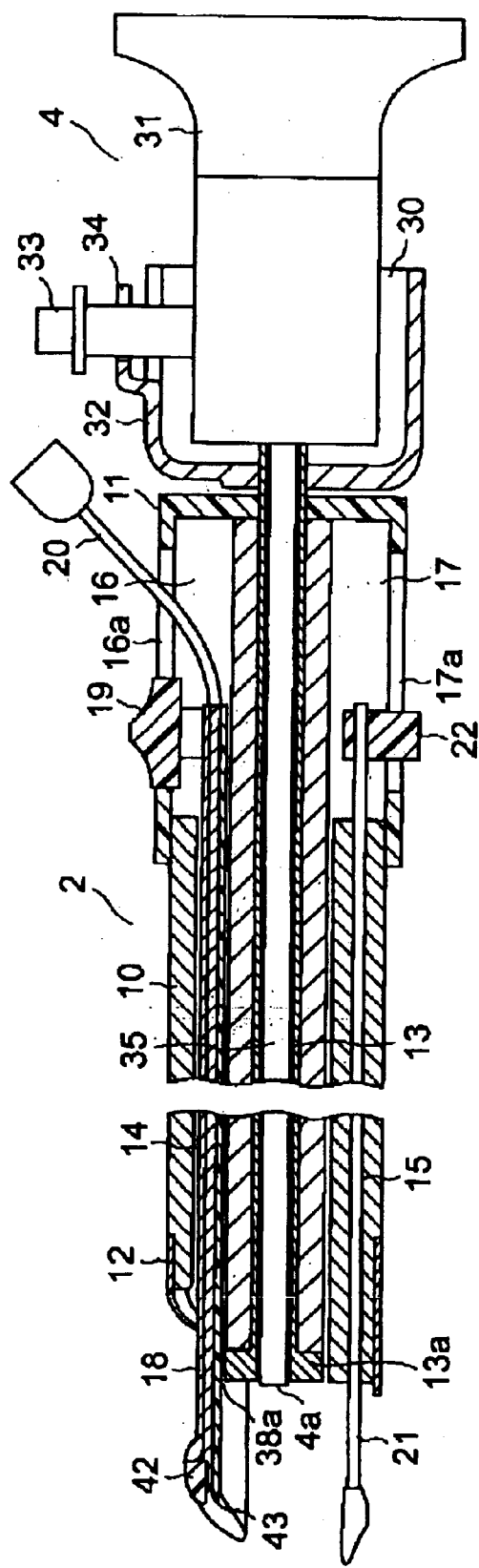
FIG. 2 is a longitudinal sectional side view of an endoscope-covering sheath through which a rigid endoscope is inserted, in the first example.
Figure 3:
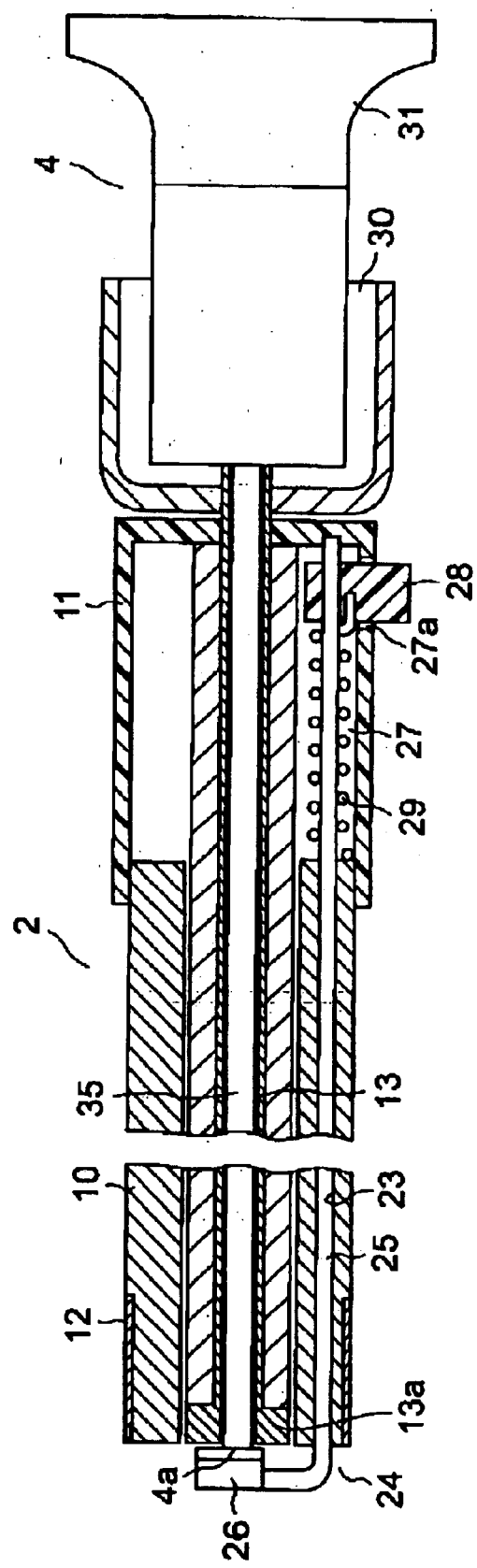
FIG. 3 is a longitudinal sectional plan view of the endoscope-covering sheath through which the rigid endoscope is inserted, in the first example.

The endoscope-covering sheath 2 is constructed as shown in FIGS. 2 and 3. A sheath body 10 has the form of a straight cylinder made of a synthetic resin material or the like, and the outer surface of the sheath body 10 is covered with a lubricating coating for improving the smoothness of insertion. A manipulating-portion cover 11 of cylindrical shape that constitutes a holding part is fitted on the proximal end of the sheath body 10, while a tip cover 12 is fitted on the distal end of the sheath body 10.

An endoscope channel 13 is disposed to extend through the central portion of the sheath body 10 along the entire length thereof. The proximal end of the endoscope channel 13 extends through the manipulating-portion cover 11 and projects toward the operator, while a flange 13a which projects from the front end of the sheath body 10 is provided at the distal end of the endoscope channel 13. In the interior of the sheath body 10, a first therapeutic instrument channel 14 is provided above the endoscope channel 13, while a second therapeutic instrument channel 15 is provided below the endoscope channel 13. Accordingly, the first therapeutic instrument channel 14 and the second therapeutic instrument channel 15 are respectively arranged at the remotest positions from each other, symmetrically about the endoscope channel 13 in the interior of the sheath body 10.

The proximal end of the first therapeutic instrument channel 14 opens up into a first slide manipulating portion 16 in the interior of the manipulating-portion cover 11, while the proximal end of the second therapeutic instrument channel 15 opens up into a second slide manipulating portion 17 in the interior of the manipulating-portion cover 11.

A bipolar cutter 18 which serves as a high-frequency therapeutic instrument to be described later is inserted through the first therapeutic instrument channel 14 in such a manner as to be movable axially back and forth, and the proximal end of the bipolar cutter 18 is provided with a therapeutic instrument manipulating portion 19 which is axially slidable within the range of a slot 16a of the first slide manipulating portion 16. A bipolar cable 20 is connected to the bipolar cutter 18, and this bipolar cable 20 is led out of the manipulating-portion cover 11 through the slot 16a.

The tip of the sheath body 10 is provided with a cutter accommodating portion 38 which communicates with the first therapeutic instrument channel 14 and can accommodate the whole of the bipolar cutter 18 when the bipolar cutter 18 is retracted. A sliding portion 38a is formed on the inner surface of the cutter accommodating portion 38 making a small clearance for the bipolar cutter 18 so that when the bipolar cutter 18 is retracted into the cutter accommodating portion 38, the sliding portion 38a comes into contact with the bipolar cutter 18 to scrape adhering matter off the bipolar cutter 18.

A blood vessel holder 21 which serves as a therapeutic instrument is inserted through the second therapeutic instrument channel 15 in such a manner as to be movable axially back and forth, and the proximal end of the second therapeutic instrument channel 15 is provided with a holder manipulating portion 22 which is axially slidable within the range of a slot 17a of the second slide manipulating portion 17.

Further, in the interior of the sheath body 10, a through-hole 23 extends axially in parallel at the side of the endoscope channel 13. A wiper rod 25 of a wiper 24 that serves as wiping means to be described later is circumferentially rotatably inserted through the through-hole 23. The distal end of the wiper rod 25 is bent into an approximately L-like shape, and the tip of the bent portion is provided with a wiper rubber 26.

The proximal end of the wiper rod 25 extends into a turning manipulating portion 27 in the interior of the manipulating-portion cover 11, and is rotatably supported by the inner wall of the manipulating-portion cover 11. A wiper manipulating portion 28 is fixed to the proximal end of the wiper rod 25, and this wiper manipulating portion 28 is turnable within the range of a slot 27a of the manipulating-portion cover 11.

Further, a torsion coil spring 29, which serves as biasing means, is made of a coil spring and is provided in the state of being fitted on the wiper rod 25 in the interior of the turning manipulating portion 27. This torsion coil spring 29 is fitted in a compressed state between an end surface of the sheath body 10 and the wiper manipulating portion 28, and biases the wiper 24 in the direction of the proximal end of the sheath body 10 and also in one circumferential direction. In addition, the torsion coil spring 29 is engaged with the end surface of the sheath body 10 and with a side surface of the wiper manipulating portion 28, and constitutes locking means for biasing the wiper rubber 26 in a direction in which the wiper rubber 26 is removed sideways from the objective lens surface 4a which constitutes the observation window of the rigid endoscope 4.

An endoscope holding portion 30 is provided on the operator side of the manipulating-portion cover 11 in the state of being fixed to the endoscope channel 13. The endoscope holding portion 30 has a cavity sufficient to accommodate at least a portion of an ocular part 31 of the rigid endoscope 4, and a cutout hole 34 is provided in a part (the top part) of a peripheral wall 32. A light guide connecting portion 33 that is provided on the ocular part 31 is inserted through and engaged with the cutout hole 34. Accordingly, when an inserting portion 35 of the rigid endoscope 4 is inserted into the endoscope channel 13 and the light guide connecting portion 33 is inserted into and engaged with the cutout hole 34 to hold the ocular part 31 on the endoscope holding portion 30, the rotation of the rigid endoscope 4 with respect to the endoscope-covering sheath 2 is prevented and the vertical attitude of the rigid endoscope 4 is set in apposition suitable for observation. Incidentally it is desirable that an endoscope holding portion 39 of the dissector 3 has the same, construction as the endoscope holding portion 30 of the endoscope-covering sheath 2.

Figure 5:
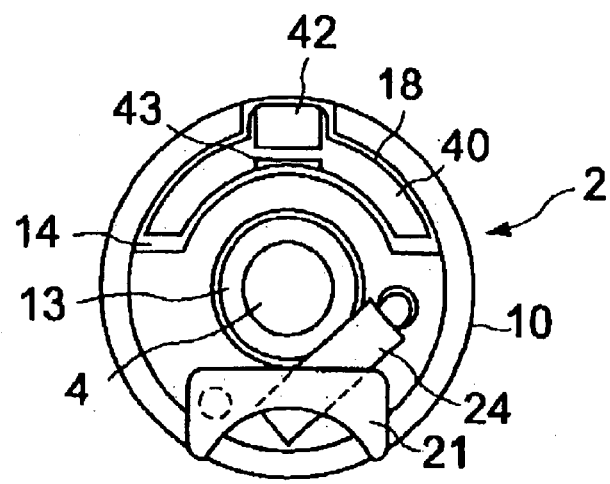
FIG. 5 is a front view of the endoscope-covering sheath of the first example.

As shown in FIGS. 4A, 4B and 5, a cutter body 40 of the bipolar cutter 18 is made of a transparent insulator such as a synthetic resin material, and has such a shape that a belt-like plate is curved into an arc shape in its cross section along the inner circumferential surface of the cutter accommodating portion 38 of the sheath body 10, and a V groove 41 cut into a V-like shape is provided at the distal end of the cutter body 40. A body-side electrode 42 is fixed to the upper side of the bottom of the V groove 41, while a cutting electrode 43 is fixed to the lower side of the bottom of the V groove 41. The body-side electrode 42 and the cutting electrode 43 are electrically connected to the bipolar cable 20.

Figures 6A, 6B:
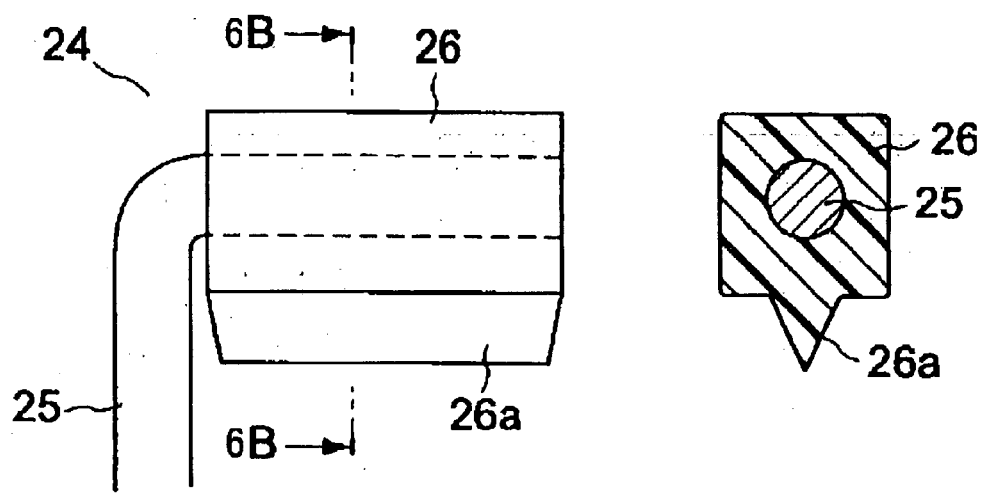
FIG. 6A is a top plan view of a wiper of the first example.
FIG. 6B is a cross-sectional view taken along line 6B—6B of FIG. 6A.

The wiper 24 is constructed as shown in FIGS. 6A and 6B. Namely, the wiper rubber 26 fixed to the distal end of the wiper rod 25 is fixed to the L-like bent portion of the wiper rod 25 by adhesion, insert molding or the like, and is disposed at right angles to the axial direction of the wipe rod 25. In one implementation, the wiper rubber 26 has a scraping portion 26a having a triangular cross section and flexibility, and is constructed to be able to turn to and fro in one plane approximately perpendicular to the rotating wiper rod 25, thereby scraping off adhering matter such as blood, mucosa and fat which adheres to the objective lens surface 4a of the rigid endoscope 4. During scraping, even if there is a step between the tip end surface of the sheath body 10 and the objective lens surface 4a, the scraping portion 26a can climb over the step and come into sliding contact with the objective lens surface 4a because the scraping portion 26a has flexibility.

Figure 7:
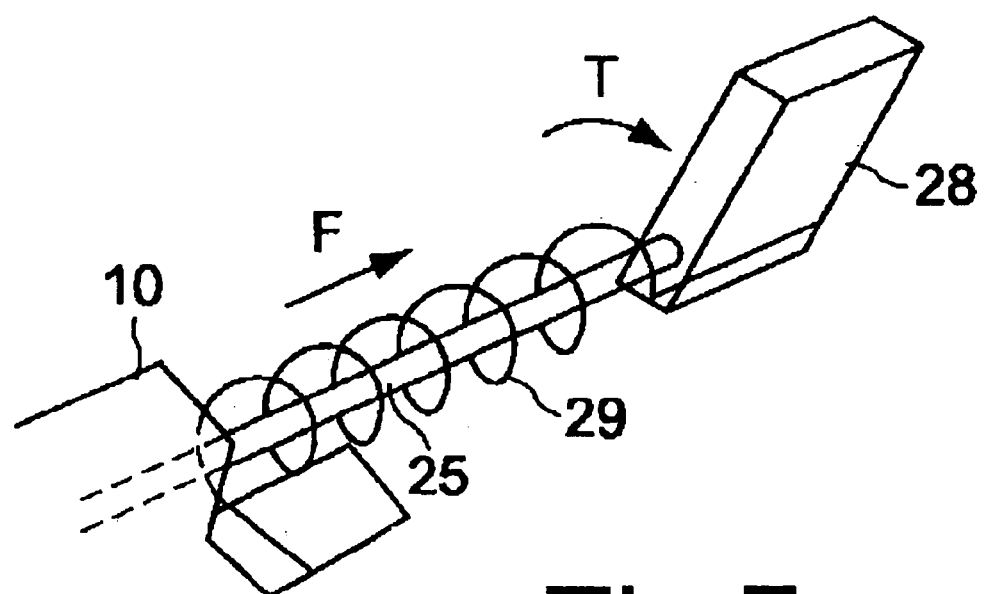
FIG. 7 is a perspective view of a wiper manipulating portion of the first example.

The torsion coil spring 29 which is made of the coil spring provided on the wiper rod 25 of the wiper 24, as shown in FIG. 7, is held against the end surface of the sheath body 10 at one end and is engaged with the side surface of the wiper manipulating portion 28 at the other end, and is in a compressed state between the sheath body 10 and the wiper manipulating portion 28. Accordingly, the torsion coil spring 29 generates torque T which acts to rotate the wiper rod 25 in the circumferential direction thereof and force F which biases the wiper rod 25 in the direction of the proximal end of the sheath body 10, whereby the wiper rubber 26 is biased to be withdrawn sideways toward the objective lens surface 4a of the rigid endoscope 4 as well as in the axial direction in which the wiper rubber 26 comes into contact with the objective lens surface 4a.

Figure 8:
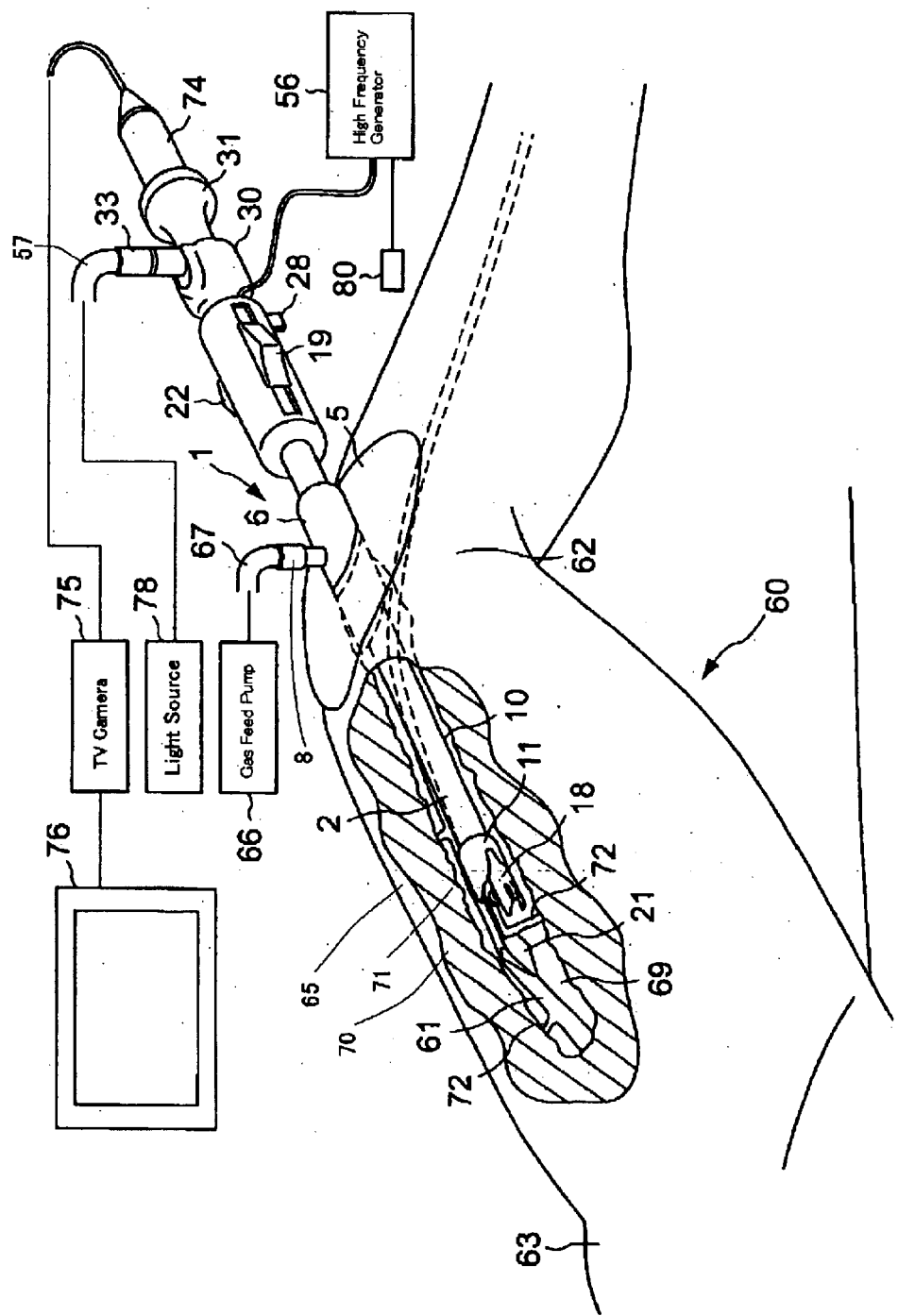
FIG. 8 is a general construction view of the state in which the endoscope-covering sheath is inserted into a cavity by using a trocar as a guide in the first example.

FIG. 8 shows the state in which the inserting portion 35 of the rigid endoscope 4 is fitted in the endoscope channel 13 of the endoscope-covering sheath 2, and the bipolar cutter 18 and the blood vessel holder 21 project from the tip of the endoscope-covering sheath 2. The bipolar cable 20 is connected to a high-frequency generating device 56, and a light guide cable 57 is connected to the light guide connecting portion 33.

The following description will be given in connection with a case where the blood vessel harvesting device constructed in the above-described manner is used to harvest the full length of a harvesting target blood vessel (hereinafter referred to simply as a blood vessel) such as a great saphenous vein which extends from the inguinal region of one of the thighs to the ankle.

Figure 9:
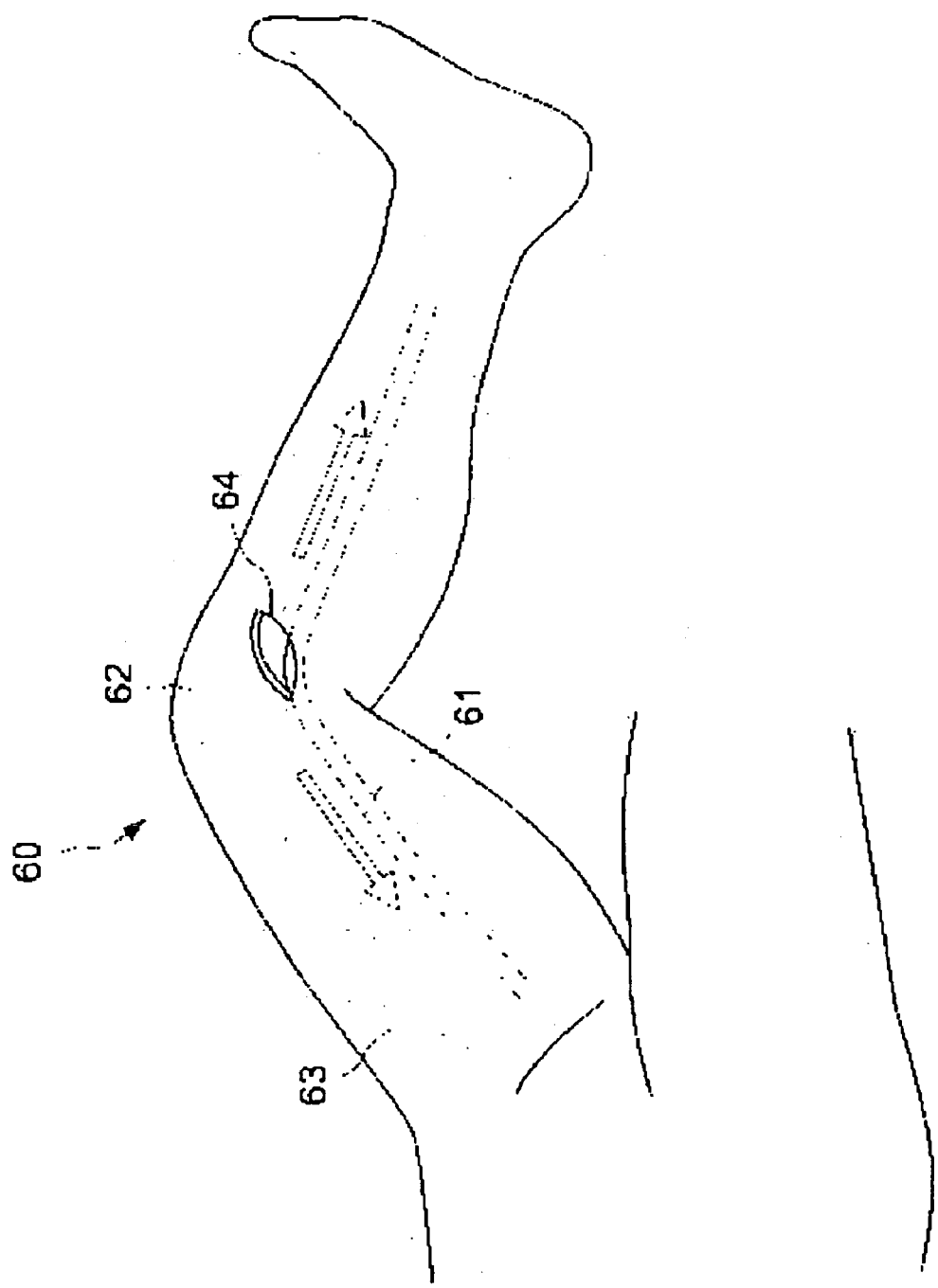
FIG. 9 is a view of the state of a leg with a dissected portion of skin.

FIG. 9 shows a leg 60, and reference numeral 61 denotes a blood vessel. First of all, when an operator is to harvest the blood vessel 61 between a knee 62 and an inguinal region 63, the operator makes an incision in skin 64 at one location of the knee 62 immediately above the blood vessel 61 by means of a scalpel or the like. The operator exposes the blood vessel 61 in the dissected portion of skin 64 by means of the dissector 3 or the like. Further, the operator dissects tissues immediately above the blood vessel 61 by means of the dissector 3 etc. so that the dissected portion of skin 64 is opened up enough to be observable with the naked eyes.

When the dissector 3 is inserted into the dissected portion of skin 64, an image of the status of dissection as seen through a dissecting portion 300 provided at the tip of the dissector 3 (FIG. 1) is, as shown in FIG. 8, picked up by a TV camera 75 via a TV camera head 74 connected to the ocular part 31 of the rigid endoscope 4 inserted in the dissect 3, and the picked-up image is displayed on a monitor 76 as a monitor image.

When the dissector 3 is inserted to a small extent, the operator inserts the guide tube 6 of the trocar 1 toward the inguinal region 63 obliquely (approximately in parallel with the blood vessel 61). When the tip 6a of the guide tube 6 is turned downward, the adhesive layer 9 on the bottom surface of the flange 5 is adhesively fixed to skin 65. In this state, the operator connects a gas fee d tube 67 connected to a gas feed pump 66 to the gas feed connecting portion 8.

Since the outer circumferential surface of the inserting tube 36 of the dissector 3 adheres closely to the gastight ring 7, the interior of the guide tube 6 and the interior of a cavity 69 are placed in a gastight state, and a gas feed passage 68 is established between the guide tube 6 and the inserting tube 36.

The light guide connecting portion 33 of the rigid endoscope 4 is connected to a light source device 78 via a light guide cable 57. Accordingly, illuminating light can be projected from a tip portion of the rigid endoscope 4 to illuminate the interior of the cavity 69. When the gas feed pump 66 is driven, a gas is fed into the cavity 69 via the gas feed tube 67, the gas feed connecting portion 8 and the gas feed passage 68, whereby the cavity 69 is expanded.

At this time, in the cavity 69, there exist subcutaneous tissue 70 and a connective tissue 71 of the blood vessel 61 that underlie the skin 65 as well as a blood vessel 61 which underlies the connective tissue 71 of the blood vessel 61. The blood vessel 61 has a plurality of side branches 72, and the branch ends of the respective side branches 72 are connected to the connective tissue 71 of the blood vessel 61. Subcutaneous fat 73 adheres to the connective tissue 71 of the blood vessel 61.

Subsequently, as shown in FIG. 8, the operator harvests the blood vessel 61 by using the endoscope-covering sheath 2. An image of the status of harvesting through the tip of the endoscope-covering sheath 2 is picked up by the TV camera 75 via the TV camera head 74 connected to the ocular part 31 of the rigid endoscope 4 inserted in the interior of the endoscope-covering sheath 2, and the picked-up image can be displayed on the monitor 76. Accordingly, the operator can clearly observe the blood vessel 61 and the side branches 72 on the monitor 76. Then, the operator inserts the cutter accommodating portion 38 into the trocar 1, and again expands the cavity 69 by feeding a gas into the cavity 69.

When the operator grips the manipulating-portion cover 11 of the endoscope-covering sheath 2 in one hand and advances the holder manipulating portion 22 by using, for example, the thumb of that hand, the blood vessel holder 21 projects from the tip cover 12 of the sheath body 10. In addition, when the operator advances the therapeutic instrument manipulating portion 19 by using the index finger of the hand in which the manipulating-portion cover 11 is gripped, the bipolar cutter 18 projects from the tip cover 12. Namely, the operator can move the blood vessel holder 21 and the bipolar cutter 18 back and forth while gripping the sheath body 10 in only one hand.

Figure 10:
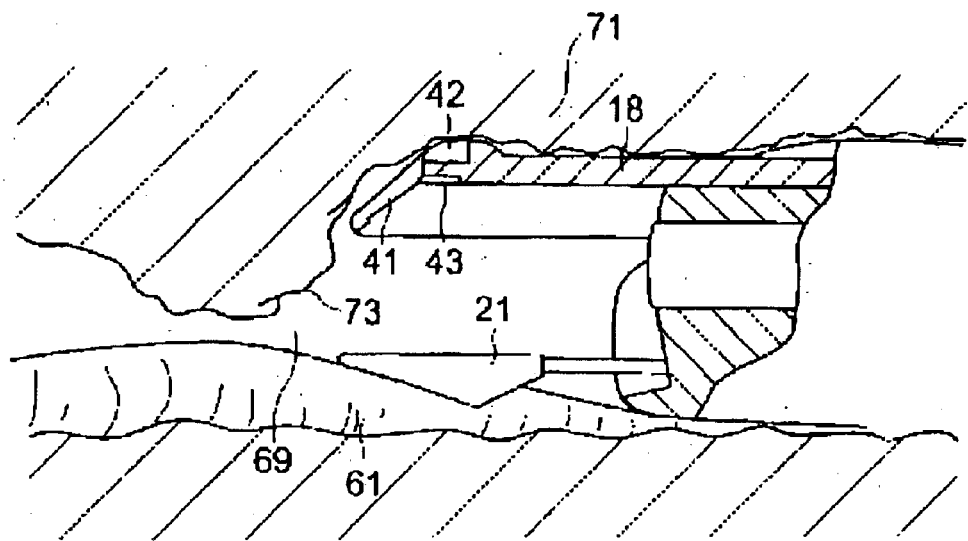
FIG. 10 is a cross-sectional view showing the state in which the cavity is treated by using the first example.

Accordingly, as shown in FIG. 10, in the case where a large amount of subcutaneous fat 73 exists in the connective tissue 71 of the blood vessel 61 in the cavity 69, the operator can expand the cavity 69 by forcing the endoscope-covering sheath 2 forward with the bipolar cutter 18 projected. At this time, the blood vessel holder 21 can be made to slide forward on the blood vessel 61 without injuring the blood vessel 61.

Figure 11:
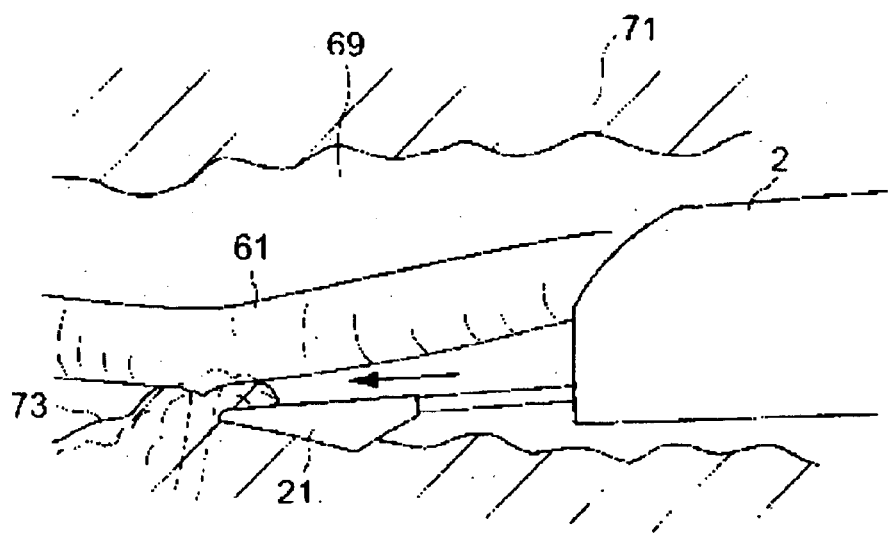
FIG. 11 is a cross-sectional view showing the state in which the cavity is treated by using the first example.

Otherwise, there is a case where some of the side branches 72 are buried in subcutaneous fat 73 as shown in FIG. 11. In this case, the operator can cut the subcutaneous fat 73 from the buried side branch 72 by projecting the blood vessel holder 21 from the endoscope-covering sheath 2 and sticking the blood vessel holder 21 into the subcutaneous fat 73 or turning the blood vessel holder 21 by turning the whole of the endoscope-covering sheath 2 in the guide tube 6 of the trocar 1 in a circumferential direction to remove the subcutaneous fat 73 from the blood vessel 61.

Figure 12:
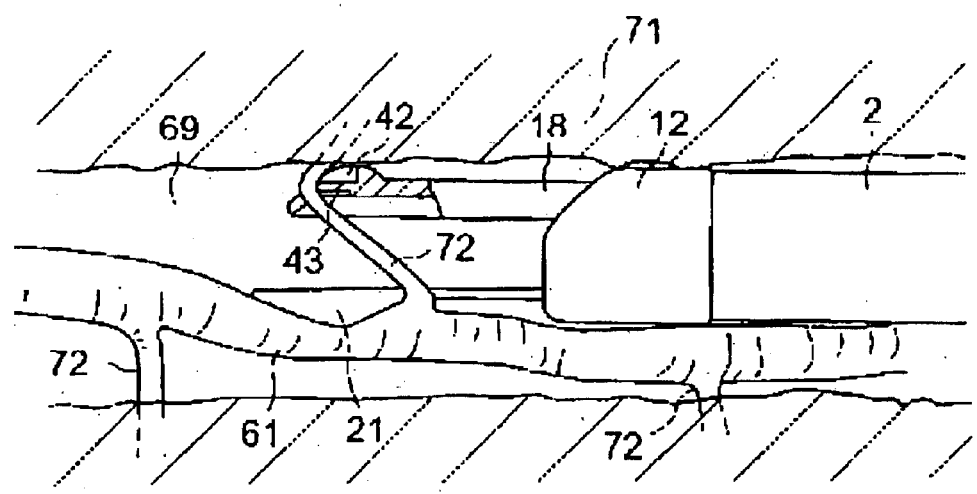
FIG. 12 is a cross-sectional view showing the state in which the cavity is treated by using the first example.

The operator further advances the blood vessel holder 21, and when the operator hooks the blood vessel holder 21 on an intermediate portion of the side branch 72 and pulls the blood vessel holder 21 toward the operator side, tension is applied to the side branch 72 as shown in FIG. 12. Then, the operator advances the bipolar cutter 18 close to the side branch 72 held by the blood vessel holder 21.

Figure 13A:
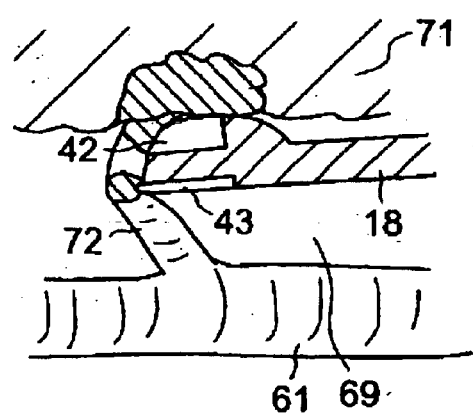
FIGS. 13A and 13B are cross-sectional views in a cavity showing the operation of a bipolar cutter of the first example.

Since the V groove 41 is provided in the tip of the bipolar cutter 18, when the operator advances the bipolar cutter 18 toward the side branch 72, the side branch 72 is drawn in the direction of the bottom of the V groove 41 by the sides of the V groove 41. Accordingly, as shown in FIG. 13A, the side branch 72 is brought into contact with the cutting electrode 43, and the body-side electrode 42 is brought into contact with the connective tissue 71 of the blood vessel 61 or the side branch 72.

Figure 13B:
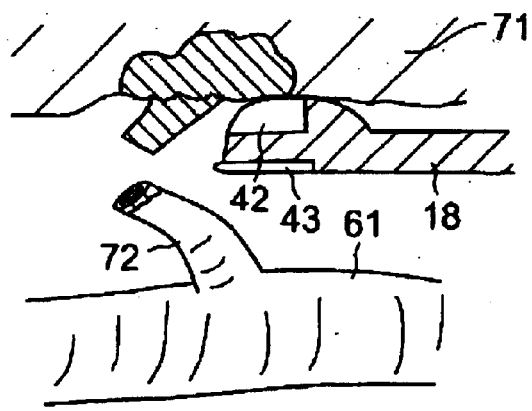

After the operator has confirmed through the monitor image that the side branch 72 has come into contact with the cutting electrode 43 and the body-side electrode 42 has come into contact with the connective tissue 71 of the blood vessel 61 or the side branch 72, the operator manipulates a foot switch 80 of the high-frequency generating device 56 to supply a high-frequency current to each of the electrodes 43 and 42. Then, the region of the connective tissue 71 of the blood vessel 61 that is in contact with the body-side electrode 42 is solidified, and the side branch 72 is cut by the cutting electrode 43. Accordingly, as shown in FIG. 13B, the portion of the blood vessel 61 that is connected to the connective tissue 71 of the blood vessel 61 by the side branch 72 is cut by the cutting of the side branch 72.

Figure 14:
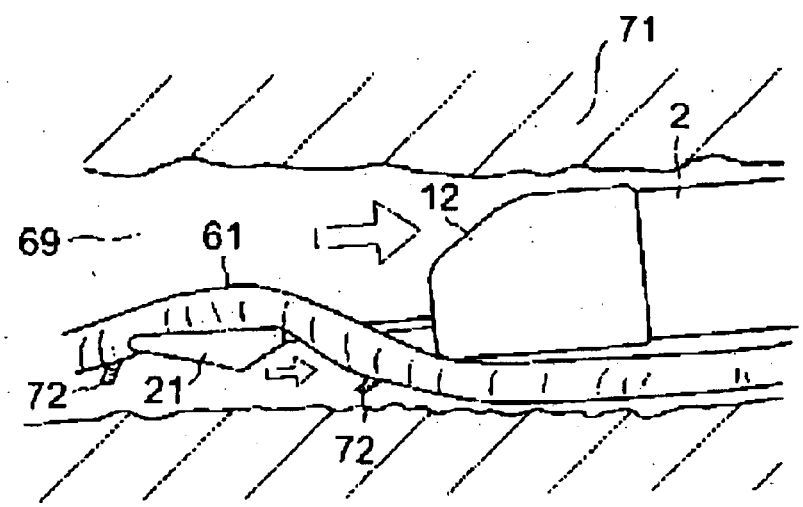
FIG. 14 is a cross-sectional view showing the state in which the cavity is treated by using the first example.

After the side branch 72 has been cut, the operator inserts the blood vessel holder 21 into an area below the blood vessel 61 and lifts the blood vessel 61 as shown in FIG. 14, and confirms through the monitor image whether the side branch 72 has been completely dissected. Furthermore, the operator, while observing the cavity 69 through the monitor image, causes the blood vessel holder 21 to approach the next one of the side branches 72, and repeats the same manipulation as the above-described one with the bipolar cutter 18 and cut the next side branch 72 to dissect the blood vessel 61 from the connective tissue 71 of the blood vessel 61.

Figure 15:
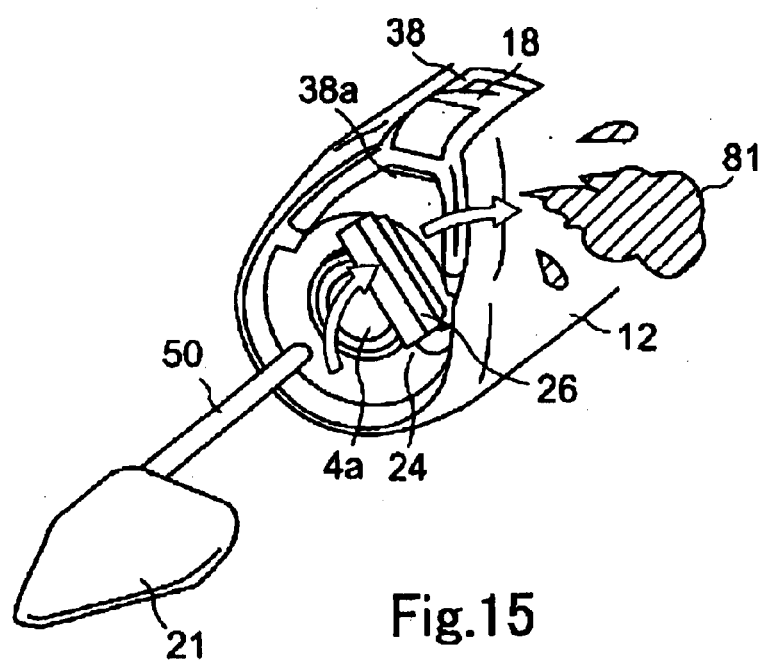
FIG. 15 is a perspective view of the tip portion of the endoscope-covering sheath of the first example.

When the manipulation of cutting each of the side branches 72 in this manner is repeated, there is a case where adhering matter 81 such as blood, mucosa and the subcutaneous fat 73 adheres to the objective lens surface 4a of the rigid endoscope 4 and hinders the viewing field of the rigid endoscope 4. In such a case, as the operator turns the wiper manipulating portion 28 against the biasing force of the torsion coil spring 29 with his fingers while gripping the manipulating-portion cover 11, the wiper 24 is made to turn by means of the wiper rod 25, as shown in FIG. 15, so that the scraping portion 26a of the wiper rubber 26 can scrape off the adhering matter 81 such as blood, mucosa and the subcutaneous fat 73 which adheres to the objective lens surface 4a.

Since the wiper 24 is biased by the torsion coil spring 29, the wiper 24 returns to its original position and withdraws from the objective lens surface 4a when the operator releases the pressure of his/her finger. Accordingly, by repeating the above-described manipulation several times, it is possible to clearly scrape off any strongly adhering matter 81 such as subcutaneous fat 73 which is not easily removed from the objective lens surface 4a. In addition, when the operator takes his/her fingers off the wiper manipulating portion 28, the wiper 24 returns to its original position and withdraws from the objective lens surface 4a, whereby the wiper 24 is prevented from hindering the viewing field of the rigid endoscope 4.

Figure 16:
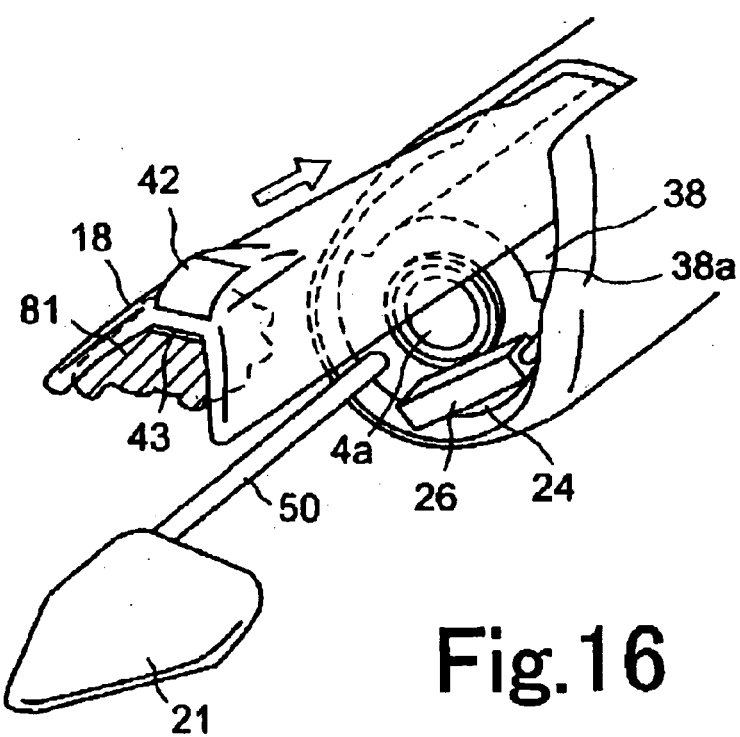
FIG. 16 is a perspective view of the tip portion of the endoscope-covering sheath of the first example.

In addition, when the manipulation of cutting each of the side branches 72 by means of the bipolar cutter 18 is, repeated, the adhering matter 81 such as mucosa and the subcutaneous fat 73 also adheres to the inner surface of the bipolar cutter 18 as shown in FIG. 16. However, when the operator moves the bipolar cutter 18 backward by means of the therapeutic instrument manipulating portion 19 and retracts the bipolar cutter 18 into the cutter accommodating portion 38 of the sheath body 10, the bipolar cutter 18 and the sliding portion 38a slide on each other because of the small clearance between the bipolar cutter 18 and the cutter accommodating portion 38, whereby the adhering matter 81 such as mucosa and the subcutaneous fat 73 which adheres to the bipolar cutter 18 is scraped off by the front end surface of the sheath body 10. Accordingly, the adhering matter 81 that adheres to the bipolar cutter 18 can be easily scraped off.

Figure 17:
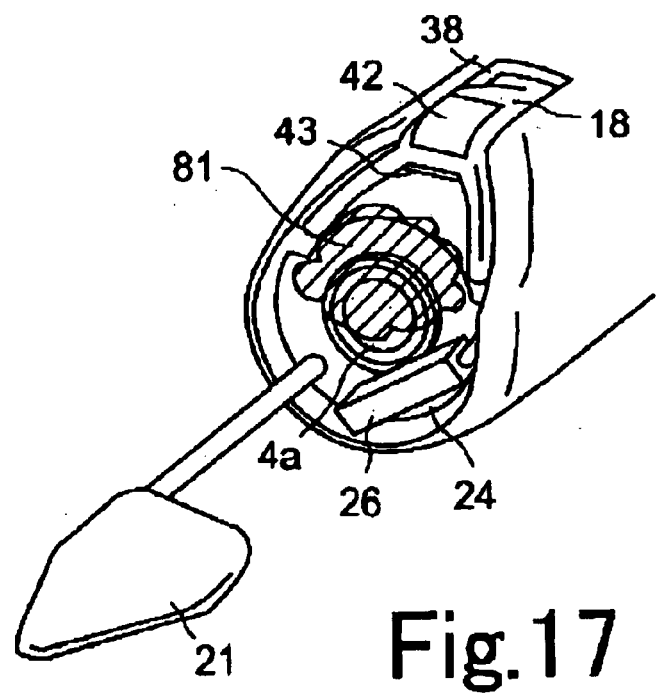
FIG. 17 is a perspective view of the tip portion of the endoscope-covering sheath of the first example.

As shown in FIG. 17, there is another case where the scraped adhering matter 81 adheres to the objective lens surface 4a of the rigid endoscope 4 and hinders the viewing field thereof. In this case as well, by turning the wiper 24 by manipulating the wiper manipulating portion 28 in the above-described manner, it is possible to scrape off the adhering matter 81 that adheres to the objective lens surface 4a.

The operator repeats the manipulation of cutting each of the side branches 72 to dissect the blood vessel 61 from the connective tissue of blood vessel 71 while repeating the manipulation of scraping off the adhering matter 81 which adheres to the bipolar cutter 18 and the manipulation scraping off the adhering matter 81 which adheres to the objective lens surface 4a, the operator completing cutting of the side branches 72 when the endoscope advances up to the inguinal region 63. Then, the operator makes an small incision in the skin in the inguinal region 63 immediately above the blood vessel 61 by means of a scalpel or the like, and draws out the blood vessel 61 through this dissected portion of skin. The operator can cut the drawn portion of the blood vessel 61, and ligates both cut ends of the blood vessel 61 with a suture.

Then, the operator performs the manipulation of harvesting the portion of the blood vessel 61 that extends from the dissected portion of skin 64 of the knee 62 toward the ankle of the lower limb 60, thereby finally harvesting a single blood vessel (about 60 cm long). The method of manipulation is basically the same as the above-described method of harvesting the portion of the blood vessel 61 that extends from the knee 62 to the inguinal region 63, and detailed explanation is omitted. The vessel which is cut at its both sides is removed from the incision dissected portion of skin 64.

FIGS. 18A and 18B show a second example according to the invention, and FIG. 18A is a longitudinal sectional side view of an endoscope-covering sheath, while FIG. 18B is an enlarged front view of the endoscope-covering sheath as viewed in the direction of arrow C. The same constituent elements as those of the first example are denoted by the same reference numerals, and the detailed explanation is omitted.

A endoscope channel 92 is provided in an off-center portion in the sheath body 91 of an endoscope-covering sheath 90, and an endoscope holding portion 93 is provided at the proximal end of the sheath body 91. The inner circumferential portion of the proximal end of the holding portion 92 is provided with a gastight member 94, and the inserting portion 35 of the rigid endoscope 4 that is inserted in the endoscope channel 92 is retained gastight.

A through-hole 95 is provided to extend axially through a thick-walled portion 91a of the sheath body 91, and the wiper rod 25 for the wiper 24 similar to that of the first example is rotatably inserted through the through-hole 95. The wiper rubber 26 is constructed to be able to turn to and fro in the same plane as that of the wiper rod 25, thereby scraping off adhering matter such as blood, mucosa and fat which adheres to the objective lens surface 4a of the rigid endoscope 4.

The torsion coil spring 29 which is made of a coil spring provided on the wiper rod 25 of the wiper 24 is held against the end surface of the sheath body 91 at one end and is engaged with the side surface of the wiper manipulating portion 28 at the other end, and is in a compressed state between the sheath body 91 and the wiper manipulating portion 28. Accordingly, the torsion coil spring 29 generates torque which acts to rotate the wiper rod 25 in the circumferential direction thereof and force which biases the wiper rod 25 in the direction of the proximal end of the sheath body 91, whereby the wiper rubber 26 is biased in the direction in which the wiper rubber 26 is to be withdrawn sideways toward the objective lens surface 4a of the rigid endoscope 4 as well as in a direction in which the wiper rubber 26 is to come into contact with the objective lens surface 4a.

Accordingly, the wiper 24 incorporated in the endoscope-covering sheath 90 has effects aid advantages similar to those of the first example.

Figure 19A:
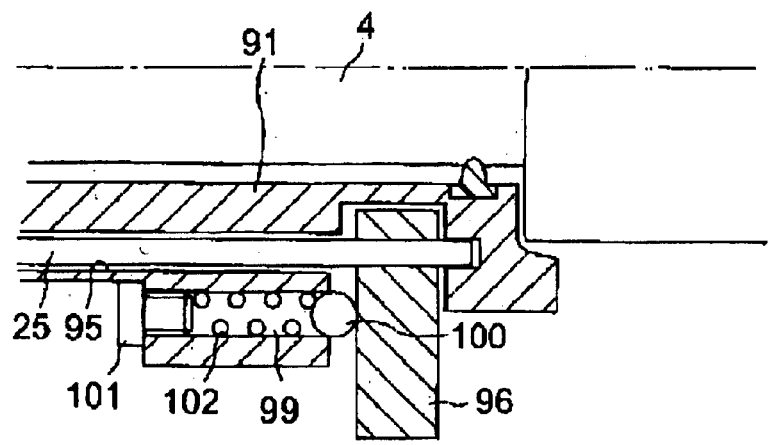
FIGS. 19A, 19B and 19C show a third example of the invention, FIG. 19A being a longitudinal sectional side view of a wiper manipulating portion, FIG. 19B being a front view of the wiper manipulating portion, and FIG. 19C being an enlarged cross-sectional view taken along line 19C—19C of FIG. 19B.
Figure 19B:
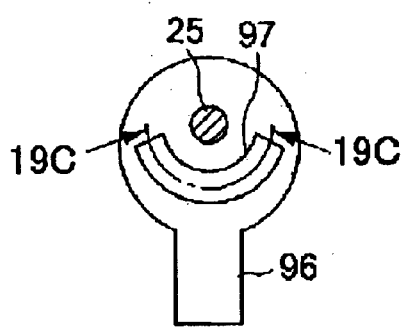
Figure 19C:
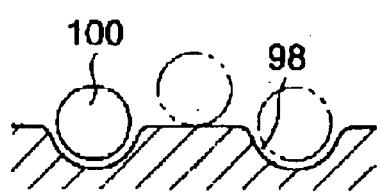

FIGS. 19A, 19B and 19C show a third example of the invention. The third example is a modification of the wiper manipulating portion of the second example. FIG. 19A is a longitudinal sectional side view of a wiper manipulating portion, FIG. 19B is a front view of the wiper manipulating portion, and FIG. 19C is an enlarged cross-sectional view taken along line 19C—19C of FIG. 19B. The same constituent elements as those of the second example are denoted by the same reference numerals, and the detailed explanation is omitted.

In the third example of the invention, a first detent mechanism is provided. The first detent mechanism is described below with reference to FIGS. 19A, 19B, and 19C. A wiper manipulating lever 96 is fixed to the proximal end of the wiper rod 25 inserted through the through-hole 95 of the sheath body 91. A cam surface 97 having an arc shape whose center of curvature is the wiper rod 25 is provided on one surface of the wiper manipulating lever 96, and detents 98 are formed on the cam surface 97.

An inserting hole 99 is provided to extend axially in the proximal end of the sheath body 91 that is opposed to the cam surface 97, and a detent ball 100 which is in contact with the cam surface 97 is provided at one end of the inserting hole 99. The detent ball 100 is inserted in the inserting hole 99 and is elastically biased against the cam surface 97 by a coil spring 102 fixed by a locking screw 101.

Accordingly, when the wiper manipulating lever 96 is turned, the detent ball 100 biased by the coil spring 102 rides along the cam surface 97 and is captured in the detents 98 in predetermined increments according to the spacing between detents 98. Accordingly, the wiper rod 25 can be locked at both ends of its movable range. Accordingly, after the objective lens surface 4a of the rigid endoscope 4 has been wiped by the wiper rubber 26, the wiper rubber 26 can be locked in the state of being withdrawn sideways toward the objective lens surface 4a, whereby the wiper rubber 26 can be prevented from hindering the viewing field of the rigid endoscope 4.

Figure 20:
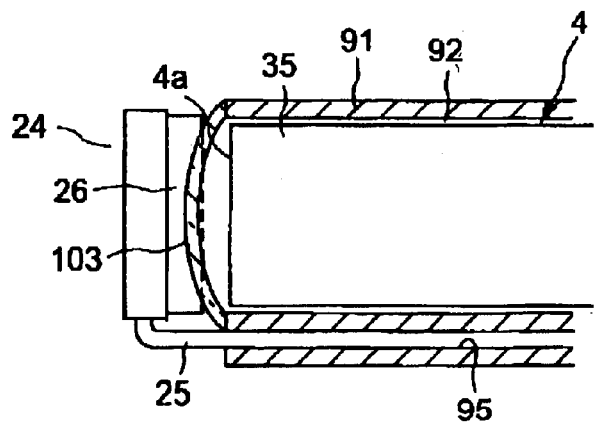
FIG. 20 is a longitudinal sectional side view of the tip portion of an endoscope-covering sheath according to a fourth example of the invention.

FIG. 20 shows a fourth example of the invention. The fourth example is a modification of the endoscope-covering sheath of the second example. The sheath body 91 of the endoscope-covering sheath 90 is provided with a transparent cover glass 103 foreclosing the tip opening of the endoscope channel 92. This cover glass 103 is formed in a convex arc shape, and the wiper rubber 26 of the wiper 24 is in sliding contact with the cover glass 103.

In this example, since the tip opening of the endoscope channel 92 is closed by the cover glass 103, the rigid endoscope 4 is prevented from directly touching and being contaminated by living tissues such as blood, mucus and fat. Accordingly, when the rigid endoscope 4 is replaced with another therapeutic instrument (not shown), the channel in the therapeutic instrument is not contaminated.

In addition, even if adhering matter such as blood, mucosa and fat adheres to this cover glass 103, the adhering matter can be easily wiped by the wiper rubber 26. The convex arcade shape is preferable to wipe out the adhering matter, but flat shape also works similarly.

Figure 22A:
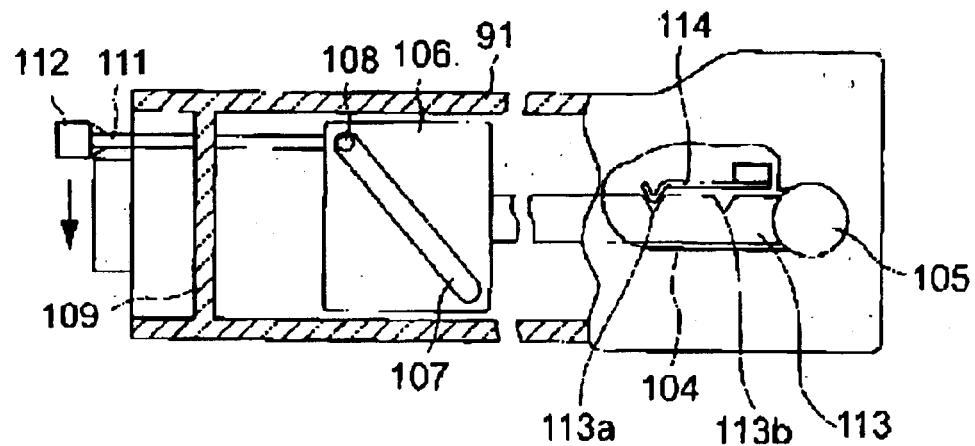
FIGS. 22A and 22B are partly cross-sectional side views of an endoscope-covering sheath, for describing the operation of the fifth example.
Figure 22B:
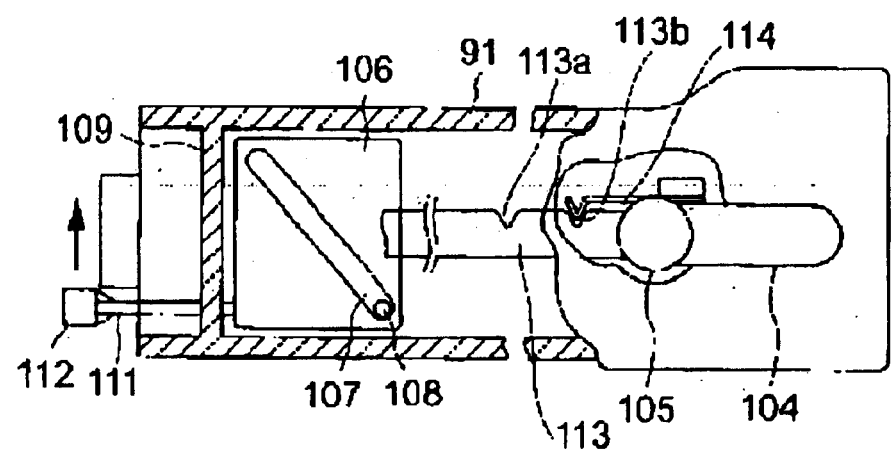
Figure 23:
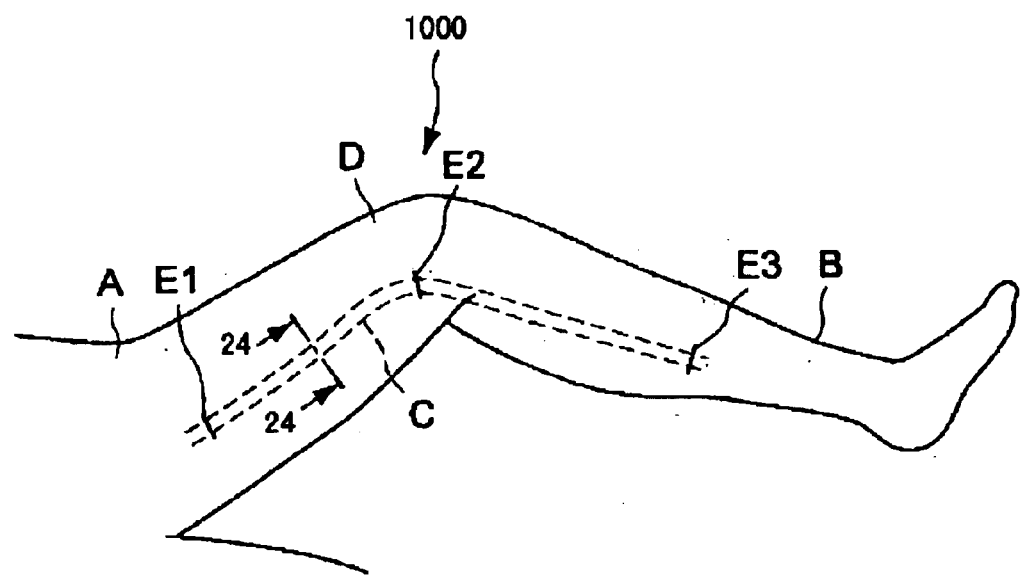
FIG. 23 is a view of the state of a leg with dissected portions of skin.
Figure 24:
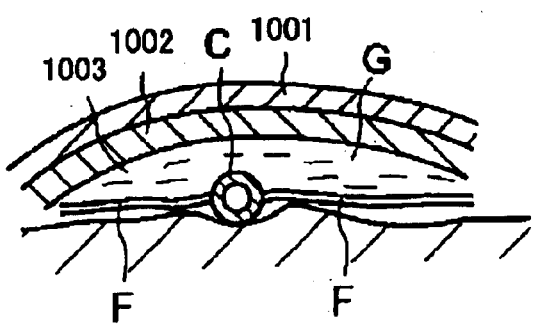
FIG. 24 is a cross-sectional view taken along line 24—24 of FIG. 23.

FIGS. 21A to 22B show a fifth example of the invention. This fifth example is a modification of the endoscope-covering sheath of the second example. FIG. 21A is a side view of an endoscope-covering sheath, FIG. 21B is a front view of the endoscope-covering sheath, and FIGS. 22A and 22B are views aiding in explaining the operation of the endoscope-covering sheath. The same constituent elements as those of the second example are denoted by the same reference numerals, and the detailed explanation is omitted.

A slot 104 that extends in the axial direction of the sheath body 91 is provided in the endoscope holding portion 93 of the sheath body 91, and a wiper manipulating portion 105 is supported for movement back and forth in this slot 104. An actuating cam 106 is provided at a position avoiding the endoscope channel 92 at the distal end of the sheath body 91, and this actuating cam 106 is connected to the wiper manipulating portion 105 via a manipulating shaft 113. A cam slot 107, which is inclined relative to the direction in which the actuating cam 106 moves back and forth, is provided in the actuating cam 106, and a cam roller 108 is movably supported in this cam slot 107.

A separating wall 109 is provided at the distal end of the sheath body 91, and a pair of guide slots 110 are vertically provided in this separating wall 109. Wiper supporting rods 111 are slidably supported in the respective guide slots 110, and one end of each of these wiper supporting rod 111 is connected to the cam roller 108, while the other end is provided with a wiper rubber 112. The opposite ends of the wiper rubber 112 are respectively supported by the wiper supporting rods 111, and the wiper rubber 112 can linearly move to and fro along the guide slots 110 to slide on the objective lens surface 4a of the rigid endoscope 4.

The fifth example is provided with a second detent mechanism, which will be described with reference to FIGS. 22A and 22B. The manipulating shaft 113 is provided with a first detent (or notch) 113a and a second detent 113b which are respectively made of axially aligned concave parts. The sheath body 91 is provided with a spring 114 which can be elastically deformed such that at least a portion of the spring comes into and out of engagement with each of the first detent 113a and the second detent 113b, thereby constituting a locking means.

Accordingly, when the wiper manipulating portion 105 is pulled toward the operator side as shown in FIG. 22A, the actuating cam 106 moves backward to force upward the cam roller 108 supported in the cam slot 107, whereby the wiper rubber 112 is moved upward by the wiper supporting rods 111. At this time, at least a portion of the spring 114 comes into engagement with the first detent 113a and the wiper rubber 112 is locked in a forced-up state.

When the wiper manipulating portion 105 is forced forward as shown in FIG. 22B, the actuating cam 106 moves forward to force downward the cam roller 108 supported in the cam slot 107, whereby the wiper rubber 112 is moved downward by the wiper supporting rods 111.

Accordingly, when the operator moves the wiper manipulating portion 105 backward and forward, the wiper rubber 112 makes linear reciprocating motion in sliding contact with the objective lens surface 4a, whereby even if adhering matter such as blood, mucosa and fat adheres to the objective lens surface 4a, the adhering matter can be easily wiped by the wiper rubber 112. When the wiper rubber 112 moves downward, at least a portion of the spring 114 comes into engagement with the second detent 113b and the wiper rubber 112 is locked in a forced-down state.

As described above, since the wiper rubber 112 is moved upward or downward and is locked in the state of being withdrawn toward the objective lens surface 4a, the wiper rubber 112 is prevented from hindering the viewing field of the rigid endoscope 4.

Although this invention has been described with respect to the examples shown in the drawings, this invention is not to be limited the above examples but, on the contrary, various modifications are possible to without departing from the spirit of this invention. All such modifications as would be obvious to one of ordinary skill in the art are intended to be included within the scope of the following claims.

What is claimed is:

1. An endoscope-covering sheath comprising:
   an elongated sheath body;
   an endoscope channel provided in the sheath body for insertion of an endoscope therein the endoscope channel having a first opening at a distal end of the sheath body;
   a wiper provided near the first opening; and
   a driving mechanism which drives the wiper to cause it to wipe a distal end of the endoscope inserted in the endoscope channel.

2. The endoscope-covering sheath according to claim 1, wherein the driving mechanism comprises a manipulating portion for manipulating the wiper at a proximal end of the sheath body, and the endoscope-covering sheath further comprises a locking mechanism which holds the wiper in a state where it does not obstruct a view through the endoscope inserted in the endoscope channel.

3. The endoscope-covering sheath according to claim 2, wherein the wiper moves transversely over the first opening.

4. The endoscope-covering sheath according to claim 3, wherein the wiper rotates in one plane.

5. The endoscope-covering sheath according to claim 3, wherein the wiper translates in one plane.

6. The endoscope-covering sheath according to claim 2, wherein the locking mechanism comprises a torsion coil spring for locking the wiper in a state where it does not obstruct a view through the endoscope.

7. The endoscope-covering sheath according to claim 2, wherein the locking mechanism comprises a detent mechanism for locking the wiper in the state of not obstructing a view through the endoscope.

8. An endoscope-covering sheath comprising:
   an elongated sheath body;
   an endoscope channel provided in the sheath body for inserting an endoscope therein;
   an opening provided at a distal end of the sheath body to allow an object to be observed through the endoscope inserted in the endoscope channel;
   a transparent cover which covers the opening; and
   a wiper provided near the transparent cover for engaging and wiping the transparent cover.

9. The endoscope-covering sheath according to claim 8, further comprising:
   a manipulating portion provided at a proximal end of the sheath body and constructed to manipulate the wiper; and
   a locking mechanism which holds the wiper in a state where it does not obstruct a view through the endoscope inserted in the endoscope channel.

10. The endoscope-covering sheath according to claim 9, wherein the locking mechanism comprises a torsion coil spring for locking the wiper in a state where it does not obstruct a view through the endoscope.

11. The endoscope-covering sheath according to claim 9, wherein the locking mechanism comprises a detent mechanism for locking the wiper in the state of not obstructing a view through the endoscope.

12. A blood vessel harvesting apparatus comprising:
    an endoscope-covering sheath insertable into a cavity; and
    an endoscope having an observation window at a distal end thereof,
    the endoscope-covering sheath including:
    a sheath body into which the endoscope can be inserted;
    a wiper provided at a distal end of the sheath body and constructed to move in contact with the observation window and wipe an outer surface of the observation window;
    a manipulating portion provided at a proximal end of the sheath body and constructed to manipulate the wiper; and
    a lock for locking the wiper in a state where it does not obstruct a view through the observation window.

13. A endoscope-covering sheath comprising:
    a sheath body insertable into a cavity;
    a wiping means provided at a distal end of the sheath body and constructed to move in one plane in contact with an observation window of an endoscope inserted in the sheath body;
    a manipulating means provided at a proximal end of the sheath body constructed to manipulate the wiper; and
    a lock means for holding the wiping means in a state where it does not obstruct a view through the endoscope.

14. The endoscope-covering sheath according to claim 13, wherein the wiping means rotates in one plane.

15. The endoscope-covering sheath according to claim 13, wherein the wiping means moves linearly in one plane.

16. The endoscope-covering sheath according to claim 13, wherein the lock means comprises a torsion coil spring for locking the wiping unit in a state where it does not obstruct a view through the endoscope.

17. The endoscope-covering sheath according to claim 13, wherein the lock means comprises a detent mechanism for locking the wiping unit in a state where it does not obstruct a view through the endoscope.

18. An endoscope-covering sheath comprising:
    an elongated sheath body;
    an endoscope channel provided in the sheath body for inserting an endoscope therein;
    an opening provided at a distal end of the sheath body for observing an object through the endoscope inserted in the endoscope channel;
    a transparent cover which covers the opening; and a wiping unit provided near the transparent cover for engaging and wiping the transparent cover.

19. The endoscope-covering sheath according to claim 18, further comprising a lock unit for holding the wiping unit in a state where it does not obstruct a view through the endoscope inserted into the sheath body.

20. The endoscope-covering sheath according to claim 19, wherein the lock unit comprises a torsion coil spring for locking the wiping unit in a state where it does not obstruct a view through the endoscope.

21. The endoscope-covering sheath according to claim 19, wherein the lock unit comprises a detent mechanism for locking the wiping unit in a state where it does not obstruct a view through the endoscope.

* * * * *